United States Patent [19]

Kataoka et al.

[11] Patent Number: 5,534,543
[45] Date of Patent: Jul. 9, 1996

[54] SYNERGISTIC INSECTICIDAL COMPOSITIONS

[75] Inventors: Masaaki Kataoka, Yaizu; Akira Wakai, Hadano; Takehiko Nakamura, Shizuoka, all of Japan

[73] Assignee: Uniroyal Chemical Company, Inc., Middlebury, Conn.

[21] Appl. No.: 459,196

[22] Filed: Jun. 2, 1995

Related U.S. Application Data

[62] Division of Ser. No. 199,233, Feb. 22, 1994, Pat. No. 5,491,168.

[30] Foreign Application Priority Data

Aug. 27, 1991 [JP] Japan ..................................... 3-238923
Oct. 8, 1991 [JP] Japan ..................................... 3-289157

[51] Int. Cl.$^6$ ........................... A01N 37/34; A01N 41/02
[52] U.S. Cl. ............................................. 514/517; 514/521
[58] Field of Search .................................... 514/521, 517

[56] References Cited

PUBLICATIONS

Sumitomo, C.A. vol. 95, (1981), 95:1918d.
Worthing et al, The Pesticide Manual, 9th ed. (1991) pp. 198, 199, 201, 202, 719, 720, 829 and 830.

*Primary Examiner*—Allen J. Robinson
*Attorney, Agent, or Firm*—Daniel Reitenbach

[57] ABSTRACT

Compounds comprised of 2-(4-tert-butylphenoxy) cyclohexyl prop-2-ynyl sulfite and a synthetic pyrethroid exhibit synergistic pesticidal activity.

10 Claims, No Drawings

SYNERGISTIC INSECTICIDAL COMPOSITIONS

This is a division of application Ser. No. 08/199,233, filed Feb. 22, 1994, now U.S. Pat. No. 5,491,168.

BACKGROUND OF THE INVENTION

Field of the Invention

This invention is directed to mixtures of propargite and synthetic pyrethroids, which exhibit synergistic activity as pesticides.

*Thrips palmi* is a transplanted insect from Southeast Asia which has caused serious damage to cucumber, watermelon, melon, eggplant and green pepper in recent years. It has no strong natural enemy, and is believed to cause more serious growth damage or fruit damage than any other known insect. Compounds such as sulbrophos, oxamil, carbosulphane, cypermethrin, pemfracalp, BMPC, DMTP, cyfulbenzron, etc. have been used in the past. However, none of them has had a sufficient protective effect.

SUMMARY OF THE INVENTION

The compositions of the present invention contain an active ingredient comprising a mixture of A) propargite, and B) a synthetic pyrethroid. The present invention also comprises a method for controlling undesirable insects which comprises applying an effective amount of a composition according to the present invention to a locus to be protected.

DETAILED DESCRIPTION OF THE INVENTION

The propargite portion of the active ingredient is a well known insecticide sold under the trademark OMITE (Uniroyal Chemical Company) and has the chemical name 2-(4-tert-butylphenoxy) cyclohexyl prop-2-ynyl sulfite. Examples of the synthetic pyrethroid active ingredient are cyfluthrin, fenpropathrin, cyhalothrin, fulvalinate, tralomethrin, etofenprox, fulcytirinate, cypermethrin, permethrin, and fenvalelate.

In the insecticide compositions of the present invention, the propargite component may be present in the amount of from 3 to 1,000 ppm, or more preferably 100–400 ppm. The synthetic pyrethroide type component may be present in the amount of from 1 to 1,000 ppm, or more preferably 10–200 ppm.

Propargite, which is one of the effective components of the insecticide offered by the present invention, shows almost no effect against minami-kiiro-azamiuma (also known as *Thrips palmi*) by itself. In addition, synthetic pyrethroide type insecticides, which is also one of the effective components of the insecticide compounds offered by the present invention, does not show sufficient effect against minami-kiiro-azamiuma by itself even in the case of cypermethrin which has obtained the Agricultural Chemical Registration in Japan. The compositions offered by the present invention give superior effectiveness which cannot be obtained by each component alone.

As it is described in the application example, common forms of agricultural agents such as aqueous solutions, emulsions, dry-flowable, flowable, or smoke agent which contain the propargite and the synthetic pyrethroide type insecticides may be prepared. Alternaterely, agents which contain the individual active ingredients are prepared and then mixed together later.

The present invention is explained in detail by reference to the following examples.

| Propargite | 30 parts |
| Tralomethrin | 1 part |
| White Carbon (Silica) | 2 parts |
| Diatmaceous Earth | 58 parts |
| Alkylbenzene sodium sulfonate | 2 parts |
| Lignin sodium sulfonate | 7 parts |

| Propargite | 30 parts |
| Tralomethrin | 1 part |
| Xylene | 44 parts |
| Dimethylformamide | 15 parts |
| Alkylbenzene calcium sulfonate | 4 parts |
| Polyoxyethylene-alkylphenylether | 6 parts |

The above components were mixed and melted to obtain a 31% emulsion.

Example 3

A mixed aqueous solution of propargite (BPPS) and synthetic pyrethroid type insecticides was diluted to the concentrations shown in Table 1, and sprayed on individually potted 20–30 cm tall greenhouse grown eggplants (kind: Kokuyo) which were severely infested by minami-kiiro-azamiuma by using a portable sprayer until the liquid started to drip from the leaves. The number of adult and larvae of minami-kiiro-azamiuma were counted before the spraying and a few days after the spraying, and its effectiveness compared with the effectiveness obtained by spraying them individually. The results are shown in Table 1.

TABLE 1

| | | Number of Insects/4 leaves[1] | | | | | | | |
| | Concentration | 0 DAT[2] | | 4 DAT | | 7 DAT | | 11 DAT | |
| Treatments[3] | (ppm) | A. | L.[4] | A. | L. | A. | L. | A. | L. |
|---|---|---|---|---|---|---|---|---|---|
| Control(No Treatment) | — | 59 | 79 | 93 | 136 | 152 | 183 | 104 | 626 |
| Propargite(Pro.) | 400 | 48 | 80 | 130 | 76 | 176 | 212 | 106 | 546 |
| Pro. + Tralomethrin | 400 + 10 | 28 | 179 | 0 | 0 | 0 | 0 | 1 | 0 |
| Tralomethrin | 10 | 31 | 108 | 17 | 71 | 59 | 123 | 44 | 64 |
| Pro. + Cypermethrin | 400 + 60 | 80 | 138 | 0 | 0 | 0 | 0 | 6 | 0 |
| Cypermethrin | 60 | 17 | 169 | 7 | 31 | 16 | 57 | 49 | 46 |
| Pro. + Cyhalothrin | 400 + 25 | 42 | 160 | 0 | 0 | 0 | 0 | 12 | 0 |
| Cyhalothrin | 25 | 26 | 132 | 35 | 153 | 69 | 185 | 39 | 65 |

TABLE 1-continued

| | | Number of Insects/4 leaves[1] | | | | | | | |
|---|---|---|---|---|---|---|---|---|---|
| | Concentration | 0 DAT[2] | | 4 DAT | | 7 DAT | | 11 DAT | |
| Treatments[3] | (ppm) | A. | L.[4] | A. | L. | A. | L. | A. | L. |
| Pro. + Permethrin | 400 + 100 | 25 | 188 | 6 | 12 | 9 | 16 | 10 | 4 |
| Permethrin | 100 | 42 | 138 | 19 | 118 | 32 | 183 | 41 | 51 |
| Pro. + Fluvalinate | 400 + 50 | 12 | 206 | 15 | 10 | 1 | 2 | 15 | 0 |
| Fluvalinate | 50 | 45 | 91 | 58 | 196 | 57 | 224 | 111 | 161 |
| Pro + Fenpropathrin | 400 + 100 | 27 | 259 | 11 | 15 | 2 | 9 | 6 | 4 |
| Fenpropathrin | 100 | 22 | 86 | 33 | 180 | 70 | 130 | 57 | 52 |
| Pro. + Etofenprox | 400 + 200 | 18 | 94 | 9 | 3 | 4 | 10 | 9 | 12 |
| Etofenprox | 200 | 33 | 70 | 56 | 71 | 62 | 244 | 77 | 131 |

[1] 2 marked leaves/pot
[2] DAT = Days after treatment
[3] Sprayed on May 27, 1991
[4] A. = Adults L. = Larvae

TABLE 2

| | | Number of Insects/4 leaves[1] | | | | | | | |
|---|---|---|---|---|---|---|---|---|---|
| | Concentration | 0 DAT[2] | | 4 DAT | | 7 DAT | | 11 DAT | |
| Treatments[3] | (ppm) | A. | L.[4] | A. | L. | A. | L. | A. | L. |
| Control(No Treatment) | — | 28 | 38 | 57 | 82 | 55 | 91 | 43 | 87 |
| Propargite(Pro.) | 400 | 28 | 38 | 19 | 37 | 15 | 46 | 33 | 72 |
| Pro. + Tralomethrin | 400 + 10 | 35 | 70 | 0 | 0 | 1 | 1 | 6 | 5 |
| Tralomethrin | 10 | 19 | 57 | 11 | 42 | 19 | 69 | 44 | 41 |
| Pro. + Cypermethrin | 400 + 60 | 60 | 102 | 0 | 0 | 3 | 4 | 2 | 1 |
| Cypermethrin | 60 | 16 | 24 | 9 | 36 | 29 | 28 | 55 | 20 |
| Pro. + Cyhalothrin | 400 + 100 | 34 | 62 | 0 | 0 | 0 | 1 | 2 | 0 |
| Cyhalothrin | 100 | 18 | 45 | 11 | 56 | 21 | 58 | 18 | 34 |
| Pro. + Cyfluthrin | 400 + 25 | 47 | 86 | 0 | 0 | 4 | 0 | 8 | 1 |
| Cyfluthrin | 25 | 27 | 97 | 8 | 28 | 35 | 104 | 45 | 17 |
| Pro. + Fluvalinate | 400 + 50 | 40 | 91 | 0 | 1 | 4 | 7 | 8 | 4 |
| Fluvalinate | 50 | 43 | 72 | 29 | 94 | 36 | 80 | 32 | 83 |

[1] 2 marked leaves/pot
[2] DAT = Days after treatment
[3] Sprayed on May 27, 1991
[4] A. = Adults L. = Larvae

Example 4

The effect of propargite (BPPS) and synthetic pyrethroid mixtures on minami-kiiro-azaiuma was studied in a manner similar to Example 3, except that the emulsion form of Example 2 was used. The results are shown in Table 2.

What is claimed is:

1. A composition useful for controlling *Thrips palmi* comprising synergistic insecticidally effective amounts of:
    (A) 2-(4-tert-butylphenoxy) cyclohexyl prop-2-ynyl sulfite; and
    (B) a synthetic pyrethroid selected from the group consisting of cyfluthrin, cyhalothrin, and tralomethrin.

2. The composition in accordance with claim 1 wherein component (A) is present in an concentration from 3–1000 ppm and component (B) is present in a concentration from 1–1000 ppm.

3. The composition in accordance with claim 1 wherein the synthetic pyrethroid is tralomethrin.

4. The composition in accordance with claim 1 wherein the synthetic pyrethroid is cyfluthrin.

5. The composition in accordance with claim 1 wherein the synthetic pyrethroid is cyhalothrin.

6. A process for controlling *Thrips palmi* which comprises applying to a locus to be protected an effective amount of a composition comprising synergistic insecticidally effective amounts of:
    (A) 2-(4-tert-butylphenoxy) cyclohexyl prop-2-ynyl sulfite; and
    (B) a synthetic pyrethroid selected from the group consisting of cyfluthrin, cyhalothrin, and tralomethrin.

7. The process in accordance with claim 6 wherein the synthetic pyrethroid is cyfluthrin.

8. The process in accordance with claim 6 wherein the synthetic pyrethroid is cyhalothrin.

9. The process in accordance with claim 6, wherein the synthetic pyrethroid is tralomethrin.

10. A process for controlling *Thrips palmi* which comprises applying to an infested locus an effective amount of a composition comprising synergistic insecticidally effective amounts of:
    (A) 2-(4-tert-butylphenoxy) cyclohexyl prop-2-ynyl sulfite; and
    (B) fenpropathrin.

* * * * *